US007072703B2

(12) United States Patent
Zhang et al.

(10) Patent No.: US 7,072,703 B2
(45) Date of Patent: Jul. 4, 2006

(54) MEDICAL DEVICE WITH FORCE MONITORING FEATURES AND METHOD THEREFOR

(75) Inventors: Yongxing Zhang, Little Canada, MN (US); Paul E. Zarembo, Vadnais Heights, MN (US); Ronald W. Heil, Jr., Roseville, MN (US)

(73) Assignee: Cardiac Pacemakers, Inc., Saint Paul, MN (US)

( * ) Notice: Subject to any disclaimer, the term of this patent is extended or adjusted under 35 U.S.C. 154(b) by 258 days.

(21) Appl. No.: 10/429,180

(22) Filed: Apr. 30, 2003

(65) Prior Publication Data

US 2004/0127889 A1 Jul. 1, 2004

Related U.S. Application Data

(60) Provisional application No. 60/437,198, filed on Dec. 31, 2002.

(51) Int. Cl.
*A61B 5/042* (2006.01)
*A61N 1/05* (2006.01)
(52) U.S. Cl. ..................... 600/374; 607/122
(58) Field of Classification Search ............... 606/108, 606/127, 129; 600/372–375, 377–383, 585; 607/115–132, 5; 604/19, 27–28
See application file for complete search history.

(56) References Cited

U.S. PATENT DOCUMENTS

| 4,979,510 A | * | 12/1990 | Franz et al. ................. 600/374 |
| 5,255,679 A | * | 10/1993 | Imran .......................... 600/375 |
| 5,300,106 A | | 4/1994 | Dahl et al. .................... 607/119 |
| 5,405,337 A | | 4/1995 | Maynard ...................... 604/281 |
| 5,589,563 A | | 12/1996 | Ward et al. ..................... 528/44 |
| 5,607,996 A | | 3/1997 | Nichols et al. | |

(Continued)

OTHER PUBLICATIONS

Measurand Inc., "S700 & S710 Joint Angle ShapeSensor Spec Sheet, S720 Miniature Joint Angle Shape Sensor, S290 12 Bit Data Acquisition System", http://www.measurand.com/products/shapesensors-literature.html, (Sep. 12, 2002), 5 pgs.

(Continued)

*Primary Examiner*—Lee S. Cohen
(74) *Attorney, Agent, or Firm*—Schwegman, Lundberg, Woessner & Kluth, P.A.

(57) ABSTRACT

A medical device for use with an implantable lead includes a force monitoring system coupled with the device. The force monitoring system monitors force placed on the medical device and/or the lead. Optionally the system compares the force with a preset limit, and notifies a user once the preset limit has been reached.

28 Claims, 8 Drawing Sheets

U.S. PATENT DOCUMENTS

| | | | |
|---|---|---|---|
| 5,683,447 A | 11/1997 | Bush et al. | 607/126 |
| 5,693,081 A | 12/1997 | Fain et al. | 907/126 |
| 5,782,841 A | 7/1998 | Ritz et al. | 606/129 |
| 5,800,497 A | 9/1998 | Bakels et al. | |
| 5,843,153 A | 12/1998 | Johnston et al. | |
| 5,938,603 A | 8/1999 | Ponzi | 600/424 |
| 6,205,359 B1 | 3/2001 | Boveja | |
| 6,215,231 B1 | 4/2001 | Newnham et al. | 310/371 |
| 6,254,568 B1 | 7/2001 | Ponzi | 604/95 |
| 6,301,507 B1 | 10/2001 | Bakels et al. | |
| 6,324,414 B1 | 11/2001 | Gibbons et al. | 600/373 |
| 6,327,492 B1 | 12/2001 | Lemelson | 600/434 |
| 6,332,089 B1 | 12/2001 | Acker et al. | 600/424 |
| 6,340,588 B1 | 1/2002 | Nova et al. | 435/287.1 |
| 6,514,237 B1 | 2/2003 | Maseda | |
| 6,522,909 B1 | 2/2003 | Garibaldi et al. | |
| 2002/0111662 A1* | 8/2002 | Iaizzo et al. | 607/119 |
| 2002/0116043 A1 | 8/2002 | Garibaldi et al. | |
| 2003/0065373 A1 | 4/2003 | Lovett et al. | 607/122 |
| 2003/0139794 A1 | 7/2003 | Jenney et al. | |
| 2004/0127889 A1 | 7/2004 | Zhang et al. | |

OTHER PUBLICATIONS

Measurand Inc., "ShapeRecorder Software User Instructions", (2002), 66 pgs.

Measurand Inc., "ShapeTape Manual", *Cautions, Description of Hardware and software options, Description and use of hardware, Instructions for ShapeWare software, Theory*, (Aug. 15, 2003), pp. i/143-114/143, I-XIX.

SRI International, "Research of Artificial Muscles", www.mmc.or.jp/info/magazine/14e/act/11/sri1.htm, (Mar. 1996), 6 pgs.

WWW.DESIGNINSITE.DK, "Material Dielectric Eastomers", web.archieve.org/web/20010306073022/www.designinsite.dk/htmsider/insptour.htm, Copyright 1996-2003 Torben Lenau This page is part of Design inSite,(Copyright 1996-2003),2 Pages.

* cited by examiner

MEDICAL DEVICE WITH FORCE MONITORING FEATURES AND METHOD THEREFOR

CROSS-REFERENCE TO RELATED APPLICATION(S)

This application claims the benefit of U.S. Provisional Application Ser. No. 60/437,198, filed Dec. 31, 2002, under 35 U.S.C. § 119(e).

TECHNICAL FIELD

The present invention relates generally to medical devices. More particularly, it pertains to medical devices with force monitoring features.

BACKGROUND

Cardiac leads are implanted in the RA, RV, epicardium, and coronary veins to treat patients with inter alia arrhythmias and patients with congestive heart failure (CHF). In certain circumstances, the lead needs to be removed such as when a lead is inoperative, becomes infected, or if the lead is no longer necessary. Removal of the chronically implanted lead can be difficult and result in trauma to the myocardium tissue or the cardiovascular system.

To implant the leads, a delivery system such as a catheter or guidewire is used. However, often it is difficult to discern the location of the lead within the patient, or determine where the lead is relative to certain locations in the heart. This leads to longer implant procedures, particularly those which require positioning of the cardiac lead within tortuous vasculature.

Other implant procedures include subcutaneous lead tunneling, such as for an epicardial pacing lead implantation, or for implanting a lead/electrode for nerve and muscle stimulation. However, lead tunneling can result in trauma to surrounding tissue if excessive force is placed on the device.

Accordingly, what is needed is a method and apparatus for minimizing trauma during the implant and explantation of cardiac leads.

SUMMARY

A method is provided including implanting a lead within a patient, where the lead is for conducting monitoring or stimulating signals through at least a portion of the patient. The method further includes placing an extracting force on the lead with a lead extraction device and at least partially extracting the lead from the patient. The lead extraction device has a force monitoring system. The method further includes monitoring the extracting force placed on the lead during extraction with the force monitoring system while placing the extracting force on the lead.

Several options for the method are as follows. For instance, in one option, the method further includes displaying information regarding the extracting force on a display on the lead extraction device after placing the extracting force on the lead. In another option, the method further includes setting a preset force limit, comparing the extracting force with the preset force limit, and providing a notification when the preset force limit is reached or surpassed. Optionally notification includes providing an audible notification.

In another embodiment, a method includes coupling a force monitoring system with a lead tunneling device, implanting at least a portion of a lead within a patient including placing a tunneling force on the lead tunneling device, tunneling through subcutaneous tissue with a tunneling device. The method further includes monitoring the tunneling force placed on the tunneling device with the force monitoring system while the tunneling force is place on the lead tunneling device, coupling the tunneling device with the portion of the lead, the lead for conducting monitoring or stimulating signals through at least a portion of the patient.

Several options for the method are as follows. For instance, in one option, the method further includes displaying information regarding the tunneling force on a display on the tunneling device. In yet another option, the method includes comparing the tunneling force with a preset force limit, and providing a notification when the preset force limit is reached or surpassed, such as a visual or audible notification.

In yet another embodiment, a method includes implanting a lead within a patient with a catheter, the catheter including a force monitoring system coupled therewith, implanting the lead includes placing an implantation force on the lead, and monitoring the implantation force placed on the lead with the force monitoring system.

Several options for the method are as follows. For instance, in one option, the method further includes measuring curvature change in the lead body. In another option, the catheter further includes a display, and the method further includes displaying information regarding the implantation force on the display on the catheter. In yet another option, the method includes comparing the implantation force with a preset force limit, and providing a notification when the preset force limit is reached or surpassed.

In yet another embodiment, a medical device is provided including a handle portion extending from a handle distal end to a handle proximal end, the handle portion coupled with an implantable lead, a force monitoring system coupled with the handle portion, the force monitoring system configured to monitor force placed on the lead as the handle portion is manipulated, and an elongate body coupled with the handle.

Several options for the medical device are as follows. For instance, in one option, the force monitoring system is removably coupled with the handle portion, and removing the force monitoring system from the handle portion does not result in damage to the force monitoring system. In another option, the handle portion further includes a display, and the display lists force monitoring information thereon. In yet another option, the medical device is a lead tunneling device, or the elongate body is a catheter, or the medical device is a lead extraction device, and the lead extraction device includes a gripping mechanism coupled with a lead. In yet another option, the force monitoring system further includes an indicator, such as a visual indicator or an audible indicator, that is activatable when a preset force condition is met.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims and their equivalents.

DESCRIPTION OF THE EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

Figure 1:
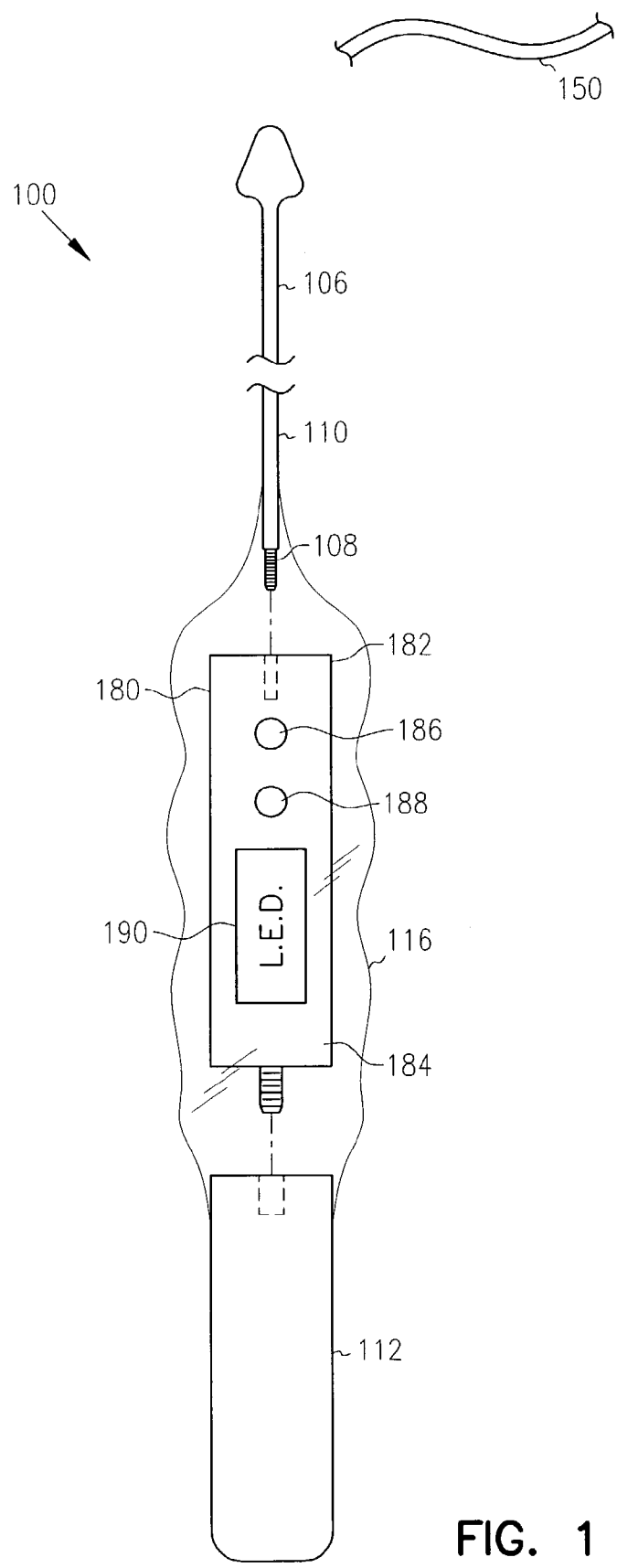
FIG. 1 illustrates a top plan view of a lead tunneling assembly constructed in accordance with one embodiment.

The subject application relates to a medical device with force monitoring features. One embodiment of such a device is illustrated in FIG. 1. A lead tunneling device 100 is provided, that allows for, for example, subcutaneous lead tunneling for a cardiac pacing lead implementation. A lead tunneling device 100, as shown in FIG. 1, can also be used, for example, when implanting a lead/electrode for nerve and muscle stimulation. The lead tunneling device 100 can be used to transport a lead 150, including a terminal connector pin, subcutaneously from a lead entrance point to a close generator implanting site with minimal trauma to the tissue where tunneling goes through. The lead tunneling device 100 further assists in preventing damage to the lead and electrode in the tunneling procedure as the force placed on the lead and electrode is monitored.

The lead tunneling device 100 includes a lead receiving unit that allows for the lead 150 to be coupled to the lead tunneling device 100. The lead tunneling device 100 further includes an elongate tunneling rod 110, and a tunneling handle 112. The tunneling rod 110 extends from a rod distal end 106 to a rod proximal end 108. The lead receiving unit couples with the tunneling rod 110 at the tunneling rod 110 distal end 106. In one option, the lead receiving unit threadingly couples with the tunneling rod 110, although other types of connection between the lead receiving unit and the tunneling rod 110 are possible, such as snap fit, or an interference fit. The lead receiving unit is designed to receive, hold and protect a lead terminal connector assembly of the lead 150 while it is transported through the patient.

The tunneling rod 110 is coupled with a force monitoring system 180. In one option, the tunneling rod 110 is coupled with the force monitoring system 180 at the tunneling rod 110 proximal end 108. In one option, the tunneling rod 110 is removably coupled with the force monitoring system 180, such as by a threaded relationship between the two. It should be noted that by removably coupled it is meant that the components can be removed from one another and coupled again to be reused, for example, after cleaning or, for example, after replacing one or more of the parts. The parts are coupled together, in one option, such that they can be reused and also uncoupled and recoupled without damage to either instrument. The tunneling rod 110 is stiff enough to "tunnel" subcutaneously and with certain flexibility to facilitate the curvature of the pectoral surface, or other regions of the body where lead tunneling is to be performed.

The force monitoring system 180 extends from a system distal end 182 to a system proximal end 184. The force monitoring system 180 is coupled with the handle 112 at the force monitoring system proximal end 184. In one option, the force monitoring system 180 is threadingly coupled with the handle 112, such that the components can be uncoupled and recoupled without damage to one or more of the components. Other options for connecting the force monitoring system 180 with the handle 112 are also available, such as a snap fit or interference fit type of coupling. The force monitoring system 180, in one option, forms a part of the handle 112, such that it can be used to manipulate the tunneling device 100. Furthermore, a clear baggie 116 is optionally placed over the force monitoring system 180, and a portion of the tunneling rod 110 and/or the handle 112. The baggie 116 assists in keeping the components clean and dry for reuse.

The force monitoring system 180 further includes, in one option, a commercially available digital or analog force gauge, including a specific force transducer. Alternative suitable force gauges include, but are not limited to, a spring loaded scale or a strain gauge, where an electric signal can be displayed on a readout, or a piezoelectric force transducer. The force transducer permits measuring tunneling forces placed on the rod 110 as the tunneling rod 110 is manipulated through a patient. The measurement of the forces can be used to minimize trauma and injury to the tissue within the patient, such that forces approaching a preset upper limit can be minimized upon notifying the technician. The force monitoring system 180 includes a mode button 186. The mode button can be used to change between English and International units, record a peak value, or to program the force monitoring system 180.

As the forces are measured by the force transducer, the force is displayed on a display 190 of the force monitoring system 180. The physician or technician can thereby monitor the amount of force being placed on the lead tunneling device as the lead tunneling device is manipulated within the patient. This will allow for reduced trauma to surrounding tissue as the lead tunneling device is manipulated through the patient.

The force monitoring system 180 further includes an indicator 188. The indicator 188 indicates when a preset force is reached such that it may be approaching limits that are harmful or other forces that are preset as maximum limits to reached. It should be noted that one or more preset forces can be input into the force monitoring system 180. Upon reaching those preset forces, the indicator 188 indicates to the technician manipulating the device that this, or one of the present limits has been reached. For instance, the indicator 188 can be a visual indicator, i.e., a light, or an audible indicator, which would include a speaker activated by a signal from the force monitoring system 180. Alternatively, it can include both. Furthermore, the force transducer is calibrated, and reset to an appropriate allowable tunneling force that would avoid injury to the patient.

Figure 2:
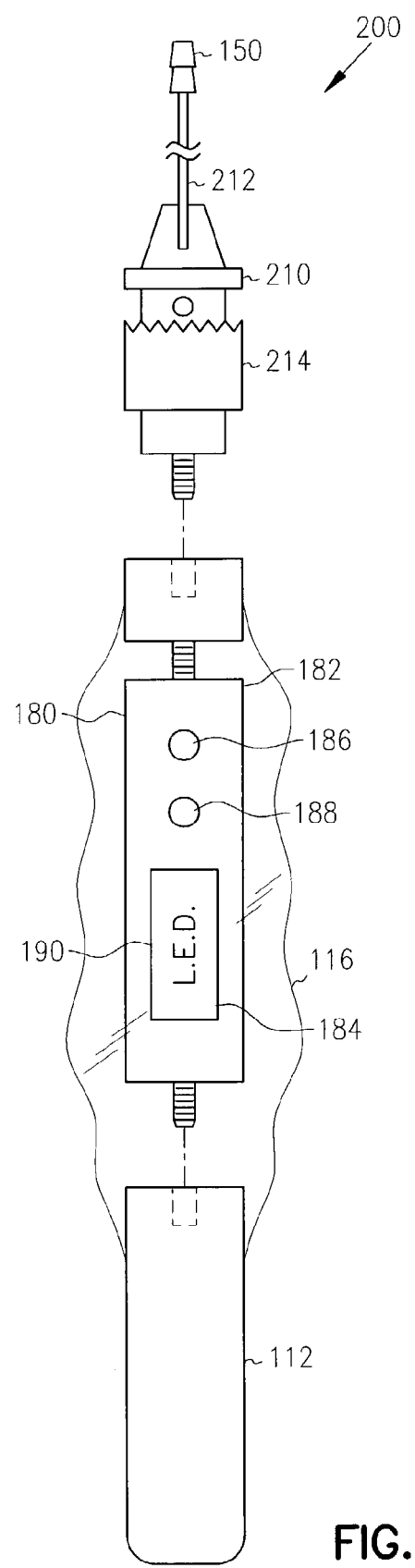
FIG. 2 illustrates a top plan view of an implantable lead extraction device constructed in accordance with one embodiment.

FIG. 2 illustrates another medical device with force monitoring features. For instance, a lead extraction tool 200 is provided with force monitoring features. The lead extraction device 200 is used for circumstances when an implanted lead needs to be removed from within a body such as, when a lead becomes inoperative, when there is an infection, or when the implanted lead is no longer necessary. While removing a chronically implanted lead can be very difficult, the lead extraction device 200 assists in removing the implanted lead while minimizing trauma to the surrounding tissue.

The lead extraction device 200 includes a lead gripping mechanism 210. The lead gripping device 210 clasps an extraction stylet 212, which is coupled with a lead 150 to be extracted. The lead gripping device 210, in one embodiment, includes a chuck 214. The chuck 214 is rotatably coupled with a force monitoring system 180, as further discussed below. The chuck 214 is rotated to grip the extraction stylet 212, and the extraction stylet 212 is coupled, for example, locked with the lead. In one option, the lead is sutured with the stylet at the distal end.

Figure 3B:
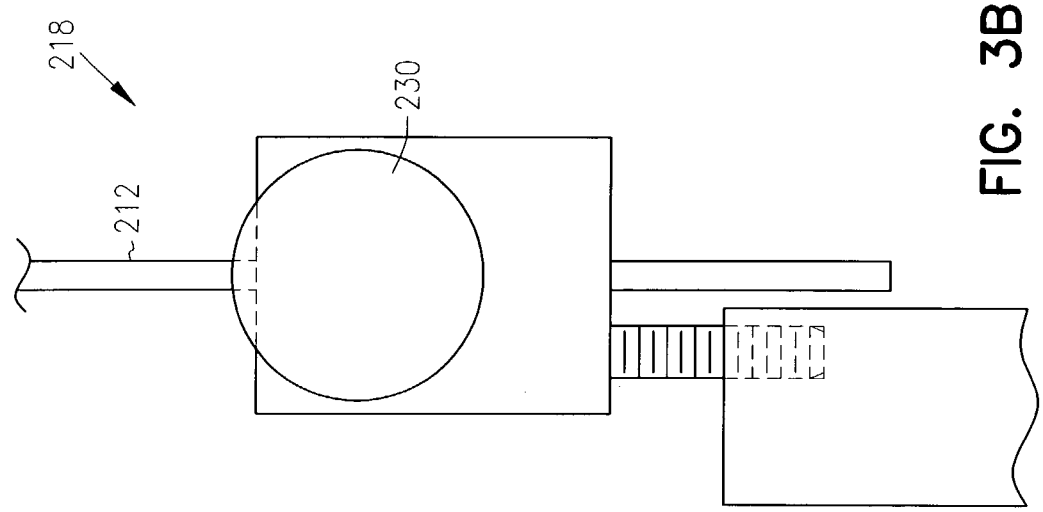
FIG. 3B illustrates a lead gripping mechanism constructed in accordance with one embodiment.
Figure 3A:
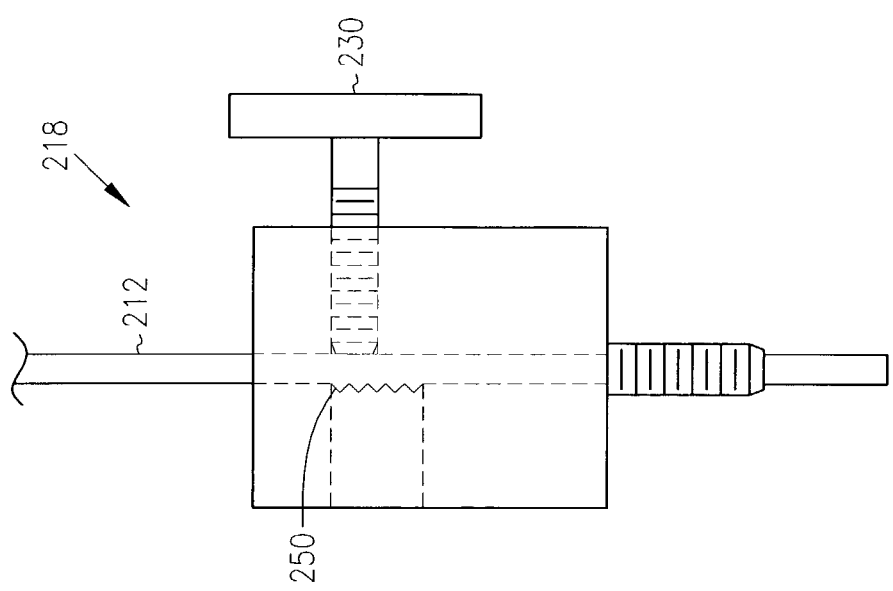
FIG. 3A illustrates a lead gripping mechanism constructed in accordance with one embodiment.

As the chuck 214 is rotated, the chuck 214 grips the extraction stylet 212. In another embodiment, as illustrated in FIGS. 3A and 3B, the lead gripping device 210 includes a thumbscrew grip mechanism 218. The thumbscrew mechanism 218 includes a thumbscrew 230 which, as it is rotated, grips the extraction stylet 212. The thumbscrew 230 approaches the extraction stylet 212, and is forced into one side of the extraction stylet 212. Optionally, a ridge 250 having increased friction is disposed opposite the thumbscrew to assist in retaining the extraction stylet 212. For instance, the ridge 250 includes several raised edges.

Figure 4:
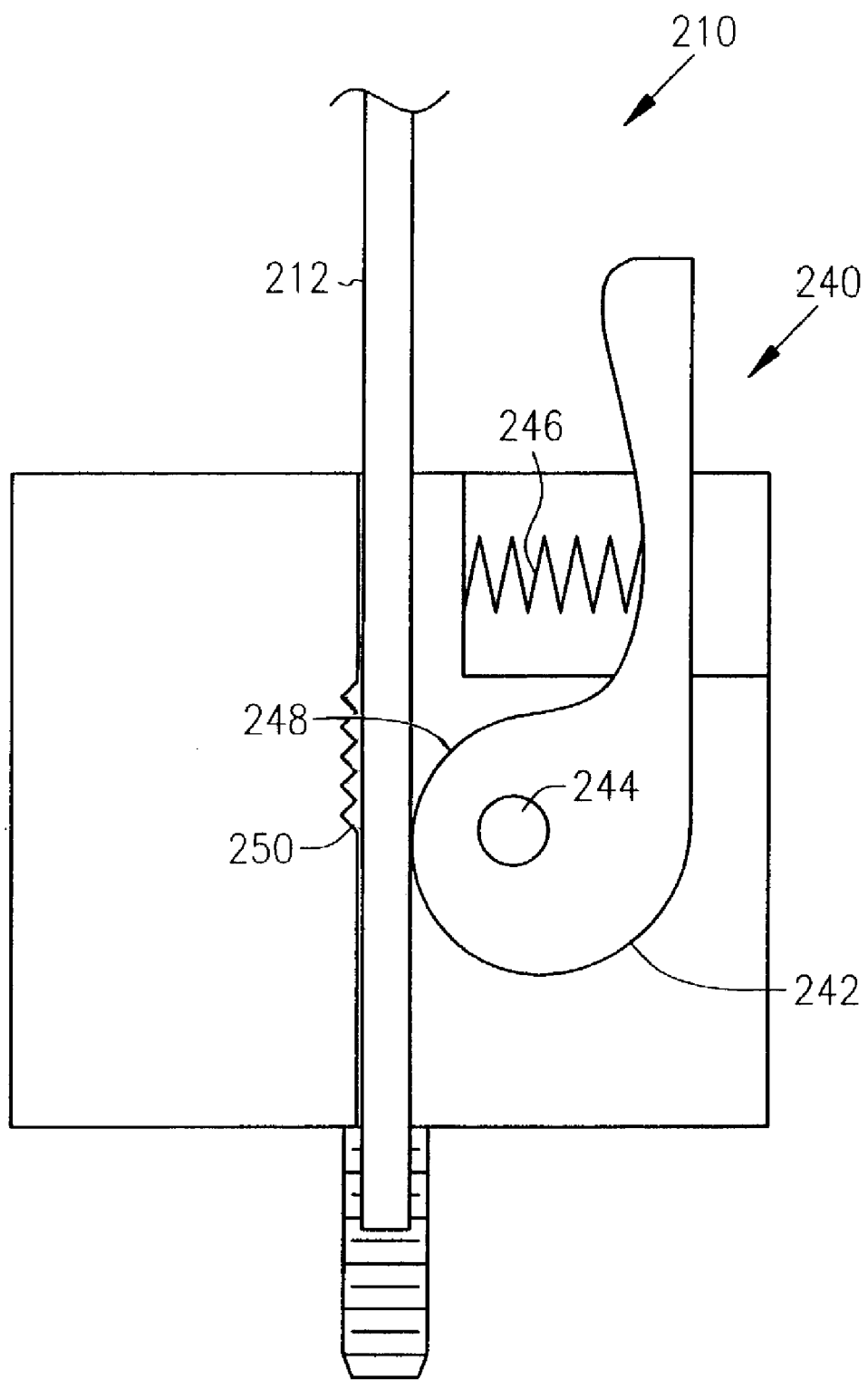
FIG. 4 illustrates a lead gripping mechanism constructed in accordance with one embodiment.

In another embodiment, as illustrated in FIG. 4, the lead gripping device 210 includes a cam-type grip mechanism 240. The cam-type grip mechanism 240 includes a cam lever 242 that is pivotably coupled about a cam pivot 244. As the cam lever is rotated about the cam pivot 244, the cam lever is pressed against a spring 246.

As the spring is compressed, a portion 248 of the cam lever 242 passes by the extraction stylet 212 and allows for the extraction stylet 212 to pass more freely through the cam-type grip mechanism 240. It follows that as the cam lever 242 is released, and a force from the spring 246 presses against the cam lever 242, the cam lever 242 engages a first side of the extraction stylet 212. Furthermore, the cam-type grip mechanism 240 includes, in one option, ridges 250 to engage an opposite side of the extraction stylet 212. The combination of the ridges 250 and the cam lever 242 when the spring properly positions the cam lever 242, the extraction stylet 212 is affirmatively gripped by the cam-type grip mechanism 240. This allows for the extraction device 200 to be used to remove and/or manipulate a lead 150 implanted within a patient. It should be noted that other variations can be provided, and are included within the scope of the claims. For instance, the spring can be other than a compression spring. Alternatively, the spring is a torsion spring, or a tensile spring. In yet another option, there can be an assembly without a spring, where is forms an interference fit.

Figure 5:
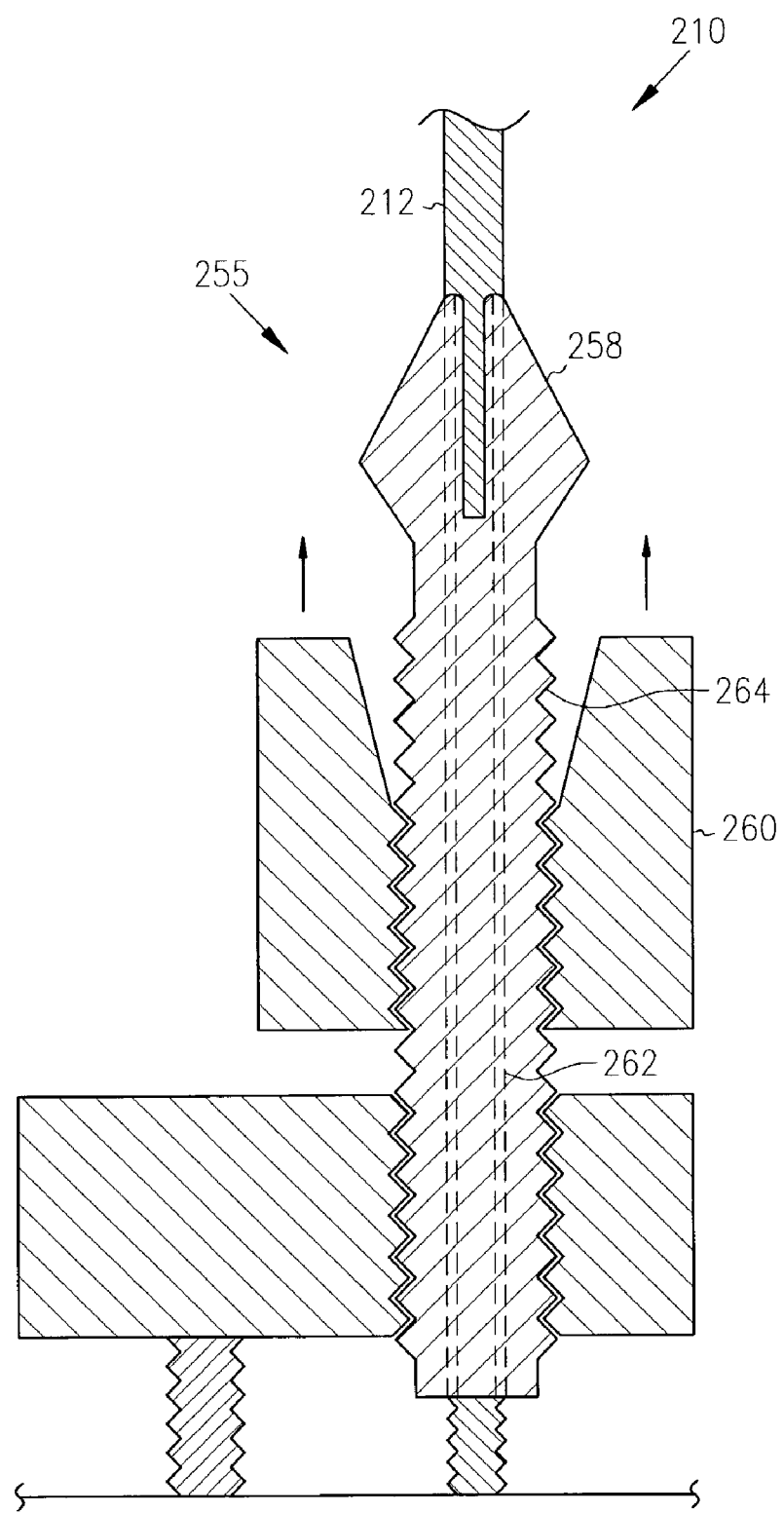
FIG. 5 illustrates a lead gripping mechanism constructed in accordance with one embodiment.

FIG. 5 illustrates another embodiment of a gripping device 210. For instance, the lead gripping device 210 optionally includes a threaded collet clamp mechanism 255. The threaded collet clamp 255 includes a split collar clamp 258 disposed around the extraction stylet 212. The threaded collet clamp 255 further includes a threaded collar 260 which includes internal threads 262 that meet with external threads 264 of the split collar clamp 258. As the internal threads 262 of the threaded collar 260 rotate about the split collar clamp 258, the threaded collar 260 travels along the split collar clamp 258 and tightens the split collar clamp onto the extraction stylet 212. Once the split collar clamp 258 is tightened onto the extraction stylet 212, the threaded collet clamp 255 can be used to extract the lead 150, while force placed on the elongate lead body is monitored. Referring again to FIG. 2, the lead gripping device 210 is removably coupled with a force monitoring system 180.

The force monitoring system 180 extends from a system distal end 182 to a system proximal end 184. The force monitoring system 180 is coupled with the handle 112 at a force monitoring system proximal end 184. In one option, the force monitoring system 180 is threadingly coupled with the handle 112, such that the components can be uncoupled and recoupled without damage to one or more of the components. Other options for connecting the force monitoring system 180 with the handle 112 are also available, such as a snap fit or interference fit type of coupling. The force monitoring system 180, in one option, forms a part of the handle 112, such that it can be used to manipulate the lead extraction device 200. Furthermore, a clear or translucent baggie 116 is optionally placed over the force monitoring system 180, and a portion of the lead extraction device 200 and/or the handle 112. The baggie 116 assists in keeping the components clean and dry for reuse.

The force monitoring system 180 includes a force transducer, such as a piezo electric gauge, a strain gauge, optical sensors, or the force gauges as discussed above and below. Alternatively, the force monitoring system 180 can use rheometric materials to measure the forces. Such materials are discussed in U.S. patent application Ser. No. 09/970,146, entitled "Medical Device Having Rheometric Materials and Method Therefor" filed on Oct. 2, 2001, and is incorporated herein by reference. The force monitoring system 180 permits measuring forces placed on the lead 150 as the lead 150 is extracted from a patient. The measurement of the forces can be used to minimize trauma and injury to the tissue within the patient, such that forces approaching a preset upper limit can be minimized upon notifying the technician. The force monitoring system 180 includes a mode button 186 as discussed above. Furthermore, the force monitoring system 180 includes an indicator 188. The indicator 188 indicates when a preset force is reached such that it may be approaching limits that are harmful or other forces that are preset as maximum limits to reached. Upon reaching those preset forces, the indicator 188 indicates to the technician manipulating the device that this preset limit has been reached. For instance, the indicator 188 can be a visual indicator, i.e., a light, or an audible indicator. Alternatively, it can include both. Furthermore, the force transducer is calibrated, and is reset to an appropriate allowable tunneling force.

As the forces are measured by the force transducer (as discussed in earlier embodiments), the force is displayed on a display 190 of the force monitoring system 180. The physician or technician can thereby monitor the amount of force being placed on the lead during the extraction procedure as the lead is being extracted from the patient. This will allow for the physician to modify the technique of extraction during the extraction procedure to minimize trauma to surrounding tissue as the lead is extracted from the patient.

Figure 6:
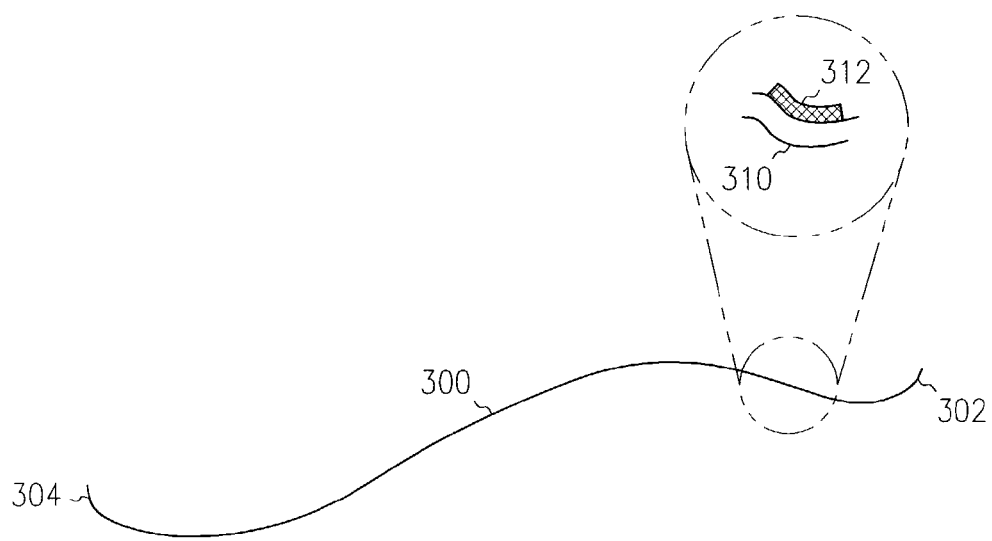
FIG. 6 illustrates a side view of a guidewire assembly constructed in accordance with one embodiment.
Figure 7:
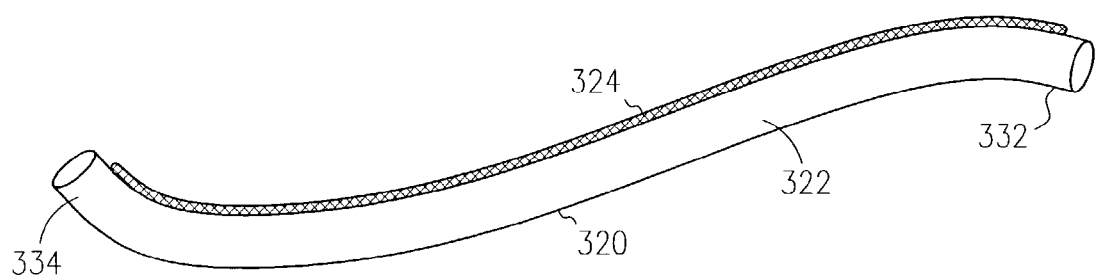
FIG. 7 illustrates a catheter assembly constructed in accordance with one embodiment.

FIGS. 6 and 7 illustrate another embodiment of a medical device including force monitoring features. FIG. 6 illustrates a guidewire that can be used with, for example, an open lumen lead, or alternatively used in conjunction with a guiding catheter, as illustrated in FIG. 7. These delivery systems are important in the implantation of cardiac leads and in other cardiovascular intervention procedures. The devices shown in FIG. 6 and FIG. 7 allow for monitoring capability of forces, pressures, or other physical characteristics of the catheter and/or the surrounding tissue.

FIG. 6 illustrates a guidewire 300 that extends from a proximal end 304 to a distal end 302. The distal end 302 is implanted into the patient and manipulated through tissue so as to allow for further manipulation of other devices thereover. The guidewire assembly 300 includes a guidewire 310 and a fiberoptic sensor 312 included therewith. The fiberoptic sensor 312, in one option, has a diameter of 0.8 mm or smaller, and can measure pressure in the range of 0–300 mm Hg. The fiberoptic sensor 312 is coupled with the guidewire 310, for example, by an adhesive, a fastener, or by co-forming the devices, for example by co-extrusion. One example of the fiberoptic sensor 312 is a SHAPE SENSOR™ package, distributed by Measurand. The fiberoptic sensor is a flexible joint angle sensor. It can be used to measure the angle of a catheter or the guidewire, or the curvature of the catheter or the guidewire, as the catheter and the guidewire assembly 300 are positioned through the patient, or as the guidewire assembly 300 is inserted through the catheter.

A regulated force supply is coupled with the fiberoptic sensor, and the output is used to determine the forces and pressures that are being placed along the guidewire 310. The information gleaned from the fiberoptic sensor 312 optionally can be displayed on an information display such as was discussed in earlier embodiments. Furthermore, the fiberoptic sensor can be used to measure the curvature and curvature change of the guidewire. In another option, the guidewire 310 or the guidewire assembly 300 is insertable into a lumen of a lead and used to measure the pressure and/or forces at a lead tip. In another option, the guidewire assembly 300 is used to measure the lead bend radii on the lead body. This information further allows for measuring the lead fatigue testing parameters. In one option, the fiberoptic sensor is smaller than 0.8 millimeters to measure a pressure of 0 to 300 mm Hg.

In another option, as shown in FIG. 7, a catheter assembly 320 includes a catheter 322 that extends from a distal end 332 to a proximal end 334. The distal end 332 of the catheter body 322 is inserted into a patient, prior to or during placement of a cardiac lead and/or an implantable lead, the guidewire assembly 300 is passed therethrough. In option, the guidewire assembly 300 includes a guidewire 310 and a fiberoptic sensor 312 (FIG. 6). In another option, the catheter assembly 320 includes a fiberoptic sensor 324.

The fiberoptic sensor 324 is coupled with the catheter 322, for example, by threading the fiberoptic sensor 324 through a lumen of the catheter 322, or by co-extruding the fiberoptic sensor 324 with the catheter 322. One example of the fiberoptic sensor 324 is a SHAPE SENSOR™ package, distributed by Measurand. The SHAPE SENSOR fiberoptic sensor is a flexible joint angle sensor. It can be used to measure the angle of the body of the guidewire, the pressure on the guidewire, pressure or forces being exerted by the guidewire, or forces placed on the catheter 322, as the catheter 322 is manipulated through the patient. A regulated force supply is coupled with the fiberoptic sensor, and the output is used to determine the forces and pressures that are being placed along the catheter 322. The information gleaned from the fiberoptic sensor 324 optionally can be displayed on an information display such as was discussed in earlier embodiments. Furthermore, the fiberoptic sensor can be used to measure the curvature and curvature change of the catheter 322. This information further allows for measuring the lead fatigue testing parameters. In one option, the fiberoptic sensor is smaller than 0.8 millimeters to measure a pressure of 0 to 300 mm Hg.

Figure 8:
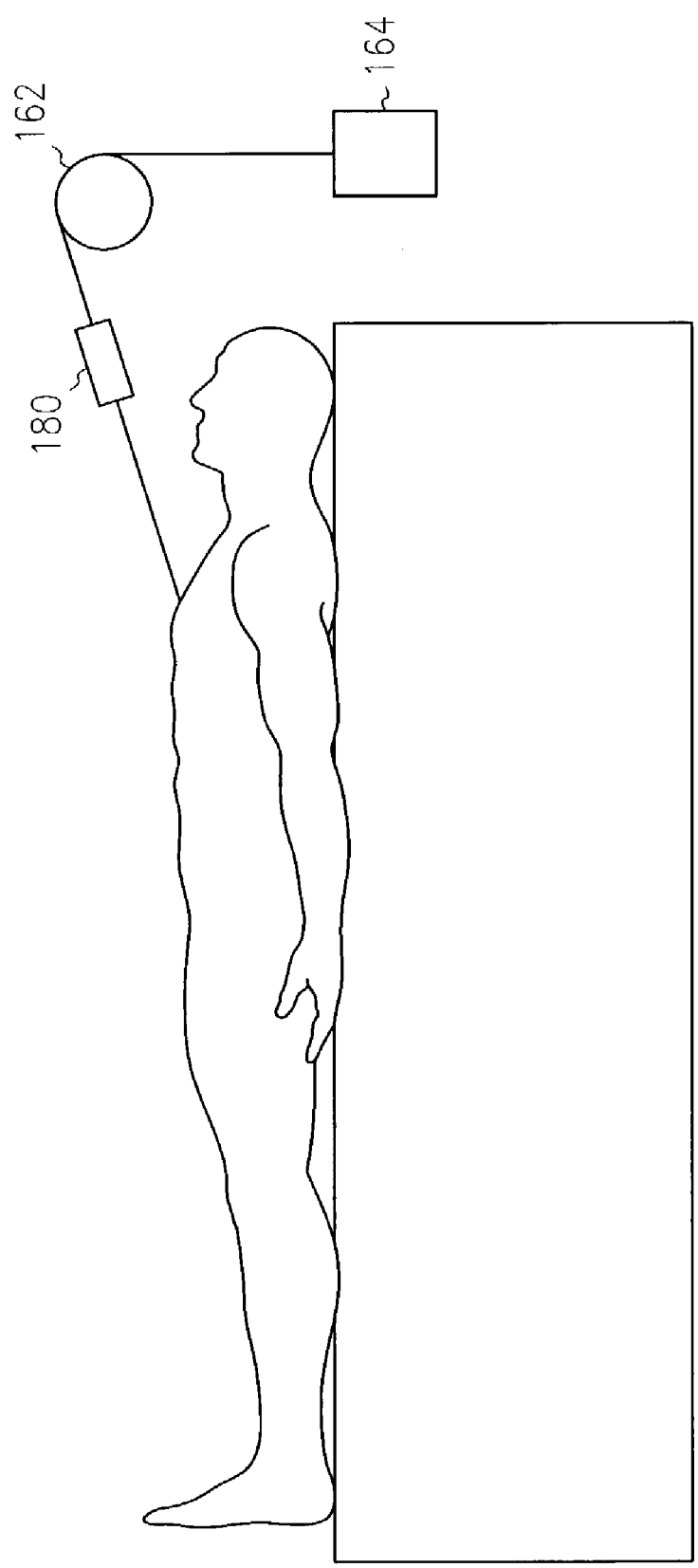
FIG. 8 illustrates a lead extraction device constructed in accordance with one embodiment.

FIG. 8 illustrates another embodiment of a lead extraction device 160. A weight 164 is coupled over a pulley 162 to a lead to be removed from a patient. The lead extraction device 160 includes a force monitoring system 180, including all of the features discussed above. As the weight hangs on the pulley, and applies a force to the lead to be extracted from the patient, the force monitoring system 180 monitors the amount of force placed on the lead and/or the patient. The force monitoring system 180 alerts the technician when certain force thresholds have been exceeded, where the technician can attend to the patient and modify the weight, as necessary. The process of extracting the lead may take several hours, which could otherwise be difficult to closely monitor the patient. The lead extraction device 160 monitors the force placed on the lead and the patient, and notifies the technician as necessary.

Figure 9:
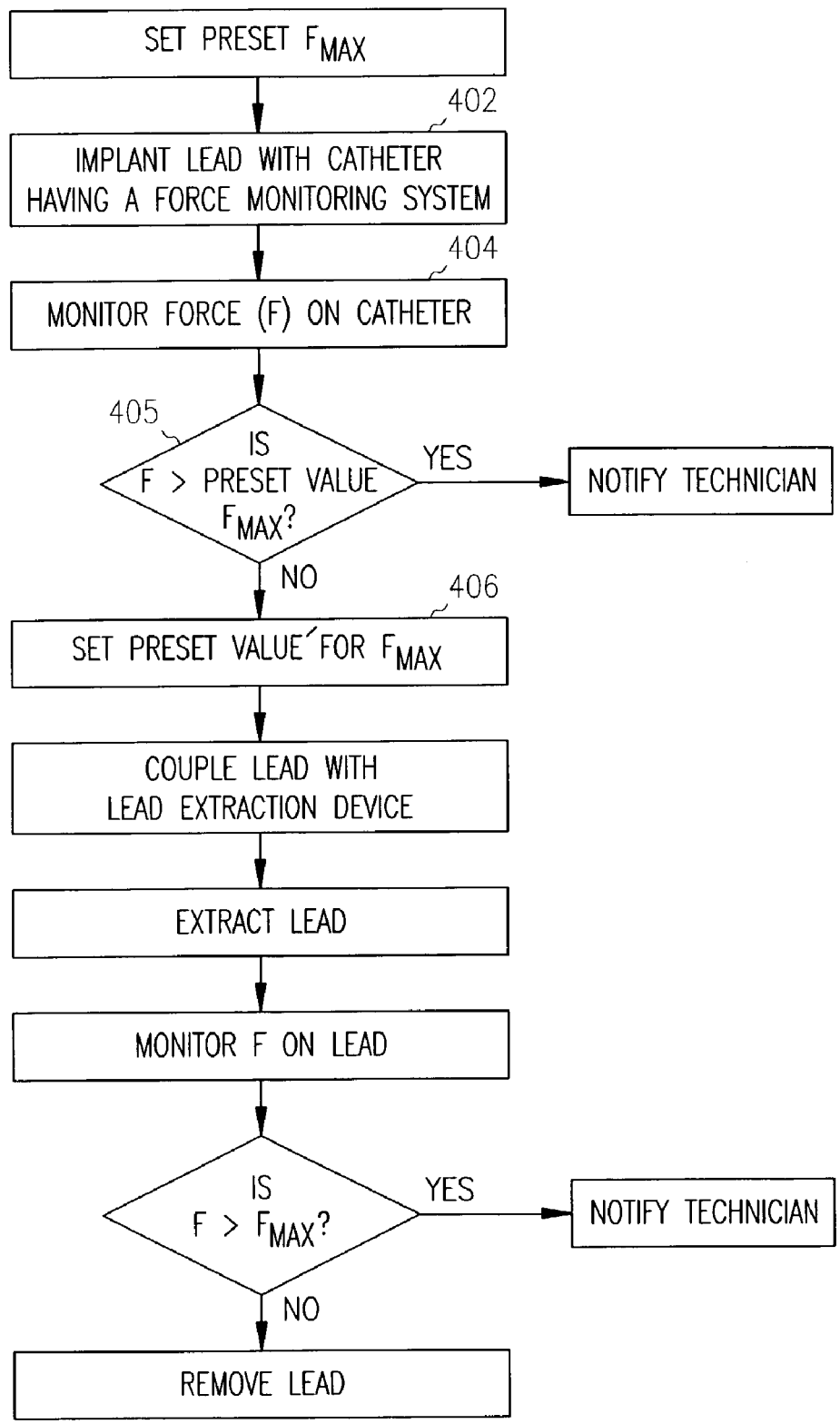
FIG. 9 illustrates a block diagram of a method for using the medical device with force monitoring features.

FIG. 9 illustrates a diagram of a method of using a medical device with force monitoring features. In a medical device including the force monitoring system, a maximum force $F_{max}$ is set for the force monitoring system. This is done in conjunction with calibration of the force monitoring system of the medical device. At 402, the medical device is used to implant the lead, for example, with the catheter as discussed with reference to FIG. 7. Optionally, the lead is implanted using the guidewire assembly of FIG. 6, and further optionally in conjunction with FIG. 7. The implantable lead is implanted within the patient, for example, using the lead tunneling device 100, as discussed earlier. At 404, the force monitoring system continuously monitors if the force placed on the medical device is greater than the preset value, $F_{max}$. If the force exceeds the preset value, $F_{max}$, at 405, the technician is notified by sending a signal to the display. It should be noted the signal can be audible, visible, or other type of signal. The force monitoring system then continues to monitor the forces placed on the lead body or the lead tip. In a further option, the force monitoring system is coupled with a lead extraction device, and at 406 the force monitoring system is calibrated on the lead extraction device and further the $F_{max}$ is preset for the force monitoring system.

The medical device and integral force monitoring system discussed above allow for the physician to conveniently monitor the pressures and forces placed on the various devices and/or cardiac leads as the devices and/or leads are manipulated through a patient. The preset force limits provide another option for assistance in preventing excessive force from being placed on tissue.

It is to be understood that the above description is intended to be illustrative, and not restrictive. Many other embodiments will be apparent to those of skill in the art upon reading and understanding the above description. It should be noted that embodiments discussed in different portions of the description or referred to in different drawings can be combined to form additional embodiments of the present invention. The scope of the invention should, therefore, be determined with reference to the appended claims, along with the full scope of equivalents to which such claims are entitled.

What is claimed is:

1. A method comprising:
   implanting a lead within a patient, the lead for conducting monitoring or stimulating signals through at least a portion of the patient;
   placing an extracting force on the lead with a lead extraction device and at least partially extracting the lead from the patient, the lead extraction device including a force monitoring system coupled therewith; and
   monitoring the extracting force placed on the lead during extraction with the force monitoring system while placing the extracting force on the lead.

2. The method as recited in claim 1, wherein the lead extraction device further includes a display, and further comprising displaying information regarding the extracting force on the display on the lead extraction device after placing the extracting force on the lead.

3. The method as recited in claim 2, further comprising setting a preset force limit, comparing the extracting force with the preset force limit, and providing a notification when the preset force limit is reached or surpassed.

4. The method as recited in claim 3, wherein providing the notification includes providing an audible notification.

5. A method comprising:
   coupling a force monitoring system with a lead tunneling device;
   coupling the lead tunneling device with a lead, the lead adapted for conducting monitoring or stimulating signals through at least a portion of a patient;
   implanting at least a portion of the lead within the patient including placing a tunneling force on the lead tunneling device, tunneling through subcutaneous tissue with the tunneling device; and
   monitoring the tunneling force placed on the tunneling device with the force monitoring system.

6. The method as recited in claim 5, wherein the tunneling device further includes a display, and further comprising displaying information regarding the tunneling force on the display on the tunneling device.

7. The method as recited in claim 5, further comprising comparing the tunneling force with a preset force limit, and providing a notification when the preset force limit is reached or surpassed.

8. The method as recited in claim 7, wherein providing a notification includes providing an audible notification.

9. A method comprising:
   implanting a lead within a patient with a catheter, the catheter including a force monitoring system coupled therewith, implanting the lead includes placing an implantation force on the lead thereby manipulating the lead through one or more portions of the patient; and
   monitoring the implantation force placed on the lead with the force monitoring system.

10. The method as recited in claim 9, further comprising measuring curvature change in the lead body.

11. The method as recited in claim 9, wherein the catheter further includes a display, and further comprising displaying information regarding the implantation force on the display on the catheter.

12. The method as recited in claim 9, further comprising comparing the implantation force with a preset force limit, and providing a notification when the preset force limit is reached or surpassed.

13. The method as recited in claim 9, further comprising disposing a guidewire assembly within the lead, the guidewire assembly including a guidewire force monitoring system, and monitoring forces with the guidewire force monitoring system.

14. A medical device comprising:
    a handle portion extending from a handle distal end to a handle proximal end, the handle portion coupled with an implantable lead;
    a force monitoring system coupled with the handle portion, the force monitoring system configured to monitor force placed on the lead as the handle portion is manipulated; and
    an elongate body coupled with the handle.

15. The medical device as recited in claim 14, wherein the force monitoring system is removably coupled with the handle portion, and removing the force monitoring system from the handle portion does not result in damage to the force monitoring system.

16. The medical device as recited in claim 14, wherein the handle portion further includes a display, the display listing force monitoring information thereon.

17. The medical device as recited in claim 14, wherein the medical device is a lead tunneling device.

18. The medical device as recited in claim 14, wherein the elongate body is a catheter.

19. The medical device as recited in claim 14, wherein the medical device is a lead extraction device, and the lead extraction device includes a gripping mechanism coupled with the lead.

20. The medical device as recited in claim 14, wherein the force monitoring system further includes an indicator activatable when a preset force condition is met.

21. The medical device as recited in claim 20, wherein the indicator is a visual indicator.

22. The medical device as recited in claim 20, wherein the indicator is an audible indicator.

23. A medical device comprising:
    an implantable lead including conductors adapted to send electric signals through a body;
    a means for gripping the implantable lead;
    a means for measuring force placed on the implantable lead while the lead is manipulated through tissue; and
    a means for notifying a technician of a force measured by the means for measuring force placed on the implantable lead.

24. The medical device as recited in claim 23, further comprising a means for comparing the force against a preset force.

25. The medical device as recited in claim 23, further comprising a handle portion, and the means for measuring force is removably coupled with the handle portion, and removing the means for measuring force from the handle portion does not result in damage to the means for measuring force.

26. The medical device as recited in claim 23, wherein the means for notifying the technician is an audible indicator.

27. The medical device as recited in claim 23, wherein the means for notifying the technician is a visible indicator.

28. The medical device as recited in claim 23, further comprising a guidewire assembly disposed within the implantable lead, the guidewire assembly including a fiber optic sensor coupled therewith.

* * * * *